(12) United States Patent
Hayashi et al.

(10) Patent No.: US 6,562,992 B2
(45) Date of Patent: May 13, 2003

(54) OPTICAL MATERIAL

(75) Inventors: Naoki Hayashi, Iwaki (JP); Shigeru Mizusawa, Iwaki (JP); Tomoyoshi Koizumi, Iwaki (JP); Katsuichi Machida, Iwaki (JP)

(73) Assignee: Kureha Kagaku Kogyo Kabushiki Kaisha, Tokyo (JP)

( * ) Notice: Subject to any disclaimer, the term of this patent is extended or adjusted under 35 U.S.C. 154(b) by 0 days.

(21) Appl. No.: 09/939,123

(22) Filed: Aug. 24, 2001

(65) Prior Publication Data

US 2002/0050587 A1 May 2, 2002

(30) Foreign Application Priority Data

Aug. 25, 2000 (JP) ........................................ 2000-255977

(51) Int. Cl.⁷ .................................................. C07F 9/40
(52) U.S. Cl. ....................... 558/177; 252/589; 558/183; 558/189
(58) Field of Search ................................ 558/177, 183, 558/189; 252/589

(56) References Cited

U.S. PATENT DOCUMENTS

| | | |
|---|---|---|
| 3,865,786 A | 2/1975 | Mueller et al. |
| 5,177,239 A * | 1/1993 | Singh et al. ............. 558/189 |
| 5,958,901 A * | 9/1999 | Dwyer et al. ............ 514/75 |

FOREIGN PATENT DOCUMENTS

| | | |
|---|---|---|
| EP | 0 783 115 A2 | 7/1997 |
| EP | 0 927 745 A1 | 7/1999 |
| GB | 1 399 106 | 6/1975 |
| JP | 09-208775 | 8/1997 |
| JP | 09-208863 | 8/1997 |
| JP | 09-208918 | 8/1997 |
| JP | 9-211220 | 8/1997 |
| JP | 2000-211220 | 8/1997 |
| JP | 2000-098130 | 4/2000 |
| WO | 99/26952 | 6/1999 |

OTHER PUBLICATIONS

El–subbagh et al (1996): J. Org. Chem. vol. 61, 890–894.*

* cited by examiner

Primary Examiner—Joseph K. McKane
Assistant Examiner—Golam M. M. Shameem
(74) Attorney, Agent, or Firm—Beyer Weaver & Thomas, LLP (57) ABSTRACT

The optical material in accordance with the present invention contains a specific phosphonate monoester compound such as monoethyl 3-methoxy butyl phosphonate, and a metal ion such as a copper ion or rare-earth metal ion. They may be contained in a solvent or resin. The use of such a specific phosphonate monoester compound improves the compatibility with a resin, whereby the metal ion can favorably be dispersed into the resin. Consequently, spectral characteristics can be improved when the optical member is formed into a resin-made optical member.

3 Claims, 6 Drawing Sheets

OPTICAL MATERIAL

BACKGROUND OF THE INVENTION

1. Field of the Invention

The present invention relates to an optical material and, more specifically, to an optical material having an absorption characteristic or emission characteristic for a specific wavelength of light (specific wavelength light) peculiar to a metal ion.

2. Related Background Art

An example of conventionally known optical materials utilizing an absorption characteristic or emission characteristic for specific wavelength light expressed by a metal ion is one including a phosphonate monoester compound represented by the following formula (2) and a copper ion:

(2)

where $X^1$ and $X^2$ indicate alkyl groups. As specific examples, commonly assigned Japanese Patent Application Laid-Open Nos. HEI 9-208775, 9-208863, 9-208918, and 9-211220 disclose phosphonate monoester copper compounds having $X^1$ and $X^2$ each of which has a carbon number of 1 to 20.

Such a phosphonate monoester copper compound has an absorption characteristic for near-infrared light peculiar to a copper ion and a transmission characteristic for visible light, thus being suitable as a material for an optical member having a near-infrared light absorptivity.

SUMMARY OF THE INVENTION

The inventors diligently studied the above-mentioned conventional phosphonate monoester copper compound from the viewpoints of transparency and optical characteristics when contained in a resin so as to form a resin-made optical member (e.g., resin sheet) which is excellent in versatility, ease of handling, and the like. As a result, there have been cases where, depending on resin bodies, a sufficient transparency is not obtained, so that they are hard to use as an optical member.

Further studies about causes thereof have revealed it desirable to further improve the compatibility with the phosphonate monoester copper compound and the resin, and that optical materials including other metal ions and phosphonate monoester compounds exhibit similar tendencies.

In view of such circumstances, it is an object of the present invention to provide an optical material which can improve the compatibility with a resin as compared with conventional ones, while having an excellent absorption characteristic or emission characteristic for specific wavelength light, thus making it possible to yield a resin-made optical member whose transparency is fully improved.

The inventors further conducted diligent studies in order to solve the problem mentioned above and, as a result, have attained a compound quite suitable for improving the compatibility, as a ligand for a metal ion such as copper ion, with a resin, thereby accomplishing the present invention. Namely, the optical material in accordance with the present invention contains a phosphonate monoester compound represented by the following formula (1):

(1)

and a metal ion.

The metal ion is not limited in particular, but is preferably an ion of an alkali metal, alkaline-earth metal, transition metal, or rare-earth metal. Preferably, the optical material in accordance with the present invention contains an ion of a transition metal or rare-earth metal among others. In the present invention, "transition metal" refers to metals having an atomic number of 21 (scandium) to 30 (zinc), 39 (yttrium) to 48 (cadmium), and 72 (hafnium) to 80 (mercury).

These metals (ions) express absorption characteristics or emission characteristics peculiar to atomic structures, so that the use of these metals yields optical materials having various characteristics. In particular, the transition metals and rare-earth metals can form an optical material excellent in functionality, since they express infrared light absorption characteristics assumed to be caused by electron transitions in d-orbit or f-orbit, or a visible light absorption or emission characteristic, whereby an optical material excellent in functionality can be formed.

Further, useful metals among these materials are sodium, potassium, magnesium, calcium, iron, manganese, nickel, cobalt, chromium, copper, neodymium, praseodymium, europium, thulium, erbium, terbium, dysprosium, samarium, lanthanum, gadolinium, holmium, and the like.

Among others, it will be particularly preferable for the optical material of the present invention if the metal ion is an ion of at least one metal of iron, manganese, nickel, cobalt, chromium, copper, neodymium, praseodymium, europium, thulium, erbium, terbium, dysprosium, samarium, lanthanum, gadolinium, and holmium.

In particular, copper can coordinate or combine with the phosphonate monoester compound, thereby favorably expressing a quite excellent infrared light absorption characteristic or visible light transmission characteristic. On the other hand, neodymium, praseodymium, europium, thulium, or erbium has a large, steep absorption wavelength peak, thus being excellent in wavelength component selectivity and tending to yield a higher emission efficiency for fluorescence and the like.

The optical member containing the phosphonate monoester compound represented by formula (1) and a copper ion, and the conventional optical material containing the phosphonate monoester compound represented by formula (2) and a copper ion were dissolved or dispersed into a monomer constituting the resin, and their optical spectra were measured. This has verified that the one in accordance with the present invention has an spectral characteristic superior to that of the conventional one.

Also proposed as other conventional optical materials are (1) one using a phosphate ester compound as a ligand for a metal ion (see, for example, commonly assigned International Publication WO9926952), (2) one using a phosphinate compound (see, for example, Japanese Patent Application Laid-Open No. 2000-98130), and (3) one using a phosphonate compound (see, for example, Japanese Patent Application Laid-Open No. 2000-7687).

The inventors also investigated and studied these optical materials from various viewpoints, and verified the superiority of the optical material in accordance with the present invention. Specifically, the optical material in accordance with the present invention exhibits an improved heat resistance as compared with the one using a phosphate ester compound in accordance with (1) and the one using a phosphinate compound in accordance with (2). Also, it has been found that the solubility or dissolution stability with respect to monomers constituting the resin drastically improves as compared with the one using a phosphonate compound in accordance with (3).

It will also be preferable if the phosphonate monoester represented by formula (1) and the copper ion are contained in a solvent or a resin. In this case, characteristics and properties corresponding to the solvent and resin used are imparted to the optical material and/or the optical member manufactured by using the same. Therefore, optical materials suitable for various uses can be obtained if the solvent and resin are selected appropriately. The present invention will be more fully understood from the detailed description given herein below and the accompanying drawings, which are given by way of illustration only and are not to be considered as limiting the present invention.

Further scope of applicability of the present invention will become apparent from the detailed description given herein after. However, it should be understood that the detailed description and specific examples, while indicating preferred embodiments of the invention, are given by way of illustration only, since various changes and modifications within the spirit and scope of the invention will be apparent to those skilled in the art from this detailed description.

DESCRIPTION OF THE PREFERRED EMBODIMENTS

In the following, preferred embodiments of the optical material in accordance with the present invention, optical members using the optical material, and the like will be explained.

Metal Ion

As for the metal ion constituting the optical material of the present invention, species of the metal are not restricted in particular, but ions of alkali metals, alkaline-earth metals, transition metals, or rare-earth metals are preferably used. These metal ions have absorption characteristics or emission characteristics peculiar to electronic structures of their respective metal atoms, whereby optical materials expressing various optical characteristics can be obtained. In particular, the transition and rare-earth metals express infrared absorption characteristics or visible light absorption or emission characteristics assumed to result from electron transitions of d-orbit and f-orbit, thereby being able to form optical materials excellent in functionality.

Specific examples of such metal ions include ions of lithium, sodium, potassium, rubidium, cesium, beryllium, magnesium, calcium, strontium, barium, scandium, titanium, vanadium, chromium, manganese, iron, cobalt, nickel, copper, zinc, yttrium, zirconium, niobium, molybdenum, ruthenium, rhodium, palladium, silver, cadmium, lanthanum, cerium, praseodymium, neodymium, promethium, samarium, europium, gadolinium, terbium, dysprosium, holmium, erbium, thulium, ytterbium, lutetium, hafnium, tantalum, tungsten, rhenium, osmium, iridium, platinum, gold, mercury, and the like.

Though the metal ion sources are not restricted in particular as long as they contain the metals, examples thereof include salts formed by these metals and organic acids such as acetic acid, formic acid, stearic acid, benzoic acid, ethyl acetoacetic acid, oxalic acid, pyrophosphoric acid, naphthenic acid, and citric acid, or inorganic acids such as sulfuric acid, hydrochloric acid, nitric acid, and hydrofluoric acid; their alkali carbonates, hydroxides, or oxides; their anhydrides, hydrates, or hydrides; and the like.

Further preferred among these metal ions are ions of sodium, potassium, magnesium, calcium, iron, magnesium, nickel, cobalt, chromium, copper, neodymium, praseodymium, europium, thulium, erbium, terbium, dysprosium, samarium, lanthanum, gadolinium, holmium, and the like. In particular, it will be further preferable if the metal ion is at least one metal ion of iron, manganese, nickel, cobalt, chromium, copper, neodymium, europium, thulium, erbium, terbium, dysprosium, samarium, lanthanum, gadolinium, and holmium.

In particular, copper exhibits favorable absorption characteristics for light in the near-infrared region (near-infrared light) and visible light transmission characteristics. More specifically, the near-infrared light is selectively absorbed due to the electron transition in the d-orbit of copper ion, whereby excellent near-infrared light absorption characteristics are expressed. As a consequence, optical materials suitable for various uses such as luminosity correction, photometry, near-infrared light and infrared light cutoff, heat ray absorption, luminance adjustment, and the like can be obtained.

Also, neodymium, praseodymium, europium, thulium, and erbium are excellent in absorption characteristics and selectivity for wavelength light peculiar to their respective ions. Specifically, their absorption peaks are large and steep. For example, a trivalent neodymium ion has a characteristic of sharply absorbing light near a wavelength of 580 nm, whereas an erbium ion has a characteristic of sharply absorbing light near a wavelength of 520 nm.

Optical materials containing such a rare-earth metal ion can form an optical member excellent in antiglare characteristic for visible light, and can form an optical member excellent in protecting eyes against laser light (having a wavelength of about 520 nm) employed in a medical or processing laser. Further, since these rare-earth metal ions, among other rare-earth metal ions, emit fluorescence with a high efficiency or emit laser, an optical material which can express an excellent light-amplifying function can be formed when they are employed.

These metal ions may be used one by one or as a mixture of two or more. Here, the amount of use of metal ions is adjusted such that their content in the optical material is preferably 0.01% to 60% by mass, more preferably 0.1% to 30% by mass, particularly favorably 0.1% to 25% by mass. If the metal ion content is less than 0.01% by mass, a sufficient absorption characteristic for specific wavelength light will be less likely to attain depending on the use and thickness of the optical material. On the other hand, if the content exceeds 60% by mass, the metal ion will be hard to dissolve or disperse in the optical material though depending on the species of metal ion.

The content of copper ion and/or rare-earth metal ion in the optical material is preferably at least 50% by mass, more preferably at least 70% by mass in the total metal ion amount, for example. As a consequence, an optical material having an optical characteristic peculiar to the copper ion and/or rare-earth metal ion can be obtained reliably.

Phosphonate Monoester Compound

The optical material in accordance with the present invention is one containing a phosphonate monoester compound represented by the following formula (1):

(1)

where $R^1$ and $R^2$ each indicate a branched, linear, or annular alkyl, alkenyl, alkynyl, aryl, or allyl group whose carbon number is 1 to 30; at least one of $R^1$ and $R^2$ having at least one hydrogen atom substituted by a halogen atom, an oxyalkyl group, a polyoxyalkyl group, an oxyaryl group, a polyoxyaryl group, an acyl group, an aldehyde group, a carboxyl group, a hydroxyl group, a (meth)acryloyl group, a (meth)acryloyloxyalkyl group, a (meth) acryloylpolyoxyalkyl group, a group having an unsaturated bond, a group having an ester bond, or a group having an aromatic ring. $R^1$ and $R^2$ may be either identical to each other or different from each other.

Examples of the phosphonate monoester compound represented by formula (1) include compounds represented by the following formulae (3)-a to (3)-d.

(3)-a (3)-b (3)-c (3)-d

If the carbon number of each of the groups $R^1$ and $R^2$ exceeds 30, it will be disadvantageous in that the compatibility becomes hard to improve sufficiently when the phosphate monoester compound represented by formula (1) is contained in the resin. As a result, it tends to be harder to disperse the metal ion into the resin favorably.

Optical Material

The optical material in accordance with the present invention contains the above-mentioned phosphate monoester compound and the above mentioned metal ion. Examples thereof include the first to fourth embodiments shown in the following.

First Embodiment

The optical material of this embodiment is manufactured when the phosphonate monoester compound represented by formula (1) and the above-mentioned metal salt to become a metal ion source are brought into contact with each other under an appropriate condition so as to react with each other. In other words, the optical material of this embodiment is constituted by a metal phosphate compound (herein after referred to as "specific phosphonate monoester metal compound" for convenience) obtained by their reaction. Specifically, the following first method, second method, and the like can be used.

First Method: A method in which the phosphonate monoester compound represented by formula (1) and the metal salt are mixed together so as to make them react with each other.

Second Method: A method in which the phosphonate monoester compound represented by formula (1) and the metal salt are caused to react with each other in an appropriate organic solvent.

The organic solvent used in the second method is not restricted in particular as long as it can dissolve or disperse the phosphonate monoester compound employed. Its examples include aromatic compounds such as benzene, toluene, and xylene; alcohols such as methyl alcohol, ethyl alcohol, and isopropyl alcohol; glycol ethers such as methyl Cellosolve and ethyl Cellosolve; ethers such as diethyl ether, diisopropyl ether, and dibutyl ether; ketones such as acetone and methyl ethyl ketone; esters such as ethyl acetate; hexane; kerosene; and petroleum ethers. Also, polymerizable organic solvents such as (meth)acrylate esters, e.g., (meth) acrylate, and aromatic vinyl compounds, e.g., styrene and α-methyl styrene, can be used.

Second Embodiment

The optical material of this embodiment is a liquid composition in which a specific phosphonate monoester metal compound is contained in a solvent. Preferably, in the liquid composition, thin films and thin layers generated upon evaporating the solvent are transparent to wavelength light other than the absorption wavelength of the metal ion. The liquid composition itself may be transparent, semitransparent, or opaque.

As the solvent, water or an organic solvent can be used. Employable as the organic solvent are alcohols such as methyl alcohol, ethyl alcohol, isopropyl alcohol, and butyl alcohol; glycol ethers such as methyl Cellosolve and ethyl Cellosolve; ethers such as diethyl ether and diisopropyl ether; ketones such as acetone, methyl ethyl ketone, methyl isobutyl ketone, and cyclohexanone; esters such as ethyl acetate, isopropyl acetate, butyl acetate, and butyl Cellosolve acetate; aromatic compounds such as benzene, toluene, and xylene; hexane; kerosene; petroleum ethers; and the like. Examples of other usable solvents include organic solvents such as (meth) acrylate esters, e.g., (meth) acrylate, and aromatic vinyl compounds, e.g., styrene and α-methyl styrene.

The expression "(meth)" in the foregoing conforms to a description method used for convenience in order to simplify the description when it is necessary to describe both of an acrylic acid or its derivative and methacrylic acid or its derivative, and thus is employed in this specification (ditto in the following).

In the case where an organic solvent is used as a solvent, the liquid composition can be manufactured when the phosphonate monoester compound and a salt acting as the metal ion source are made to react with each other in an appropriate organic solvent, for example.

The organic solvent is not restricted in particular as long as it can dissolve or disperse the phosphonate monoester composition employed. Examples thereof include aromatic compounds such as benzene, toluene, and xylene; furans such as tetrahydrofuran or furan derivatives; alcohols such as methyl alcohol, ethyl alcohol, and isopropyl alcohol; glycol ethers such as methyl Cellosolve and ethyl Cellosolve; ethers such as diethyl ether, diisopropyl ether, and dibutyl ether; ketones such as acetone and methyl ethyl ketone; esters such as ethyl acetate; hexane; kerosene; and petroleum ethers. Also, polymerizable organic solvents such as (meth) acrylate esters, e.g., (meth) acrylate, and aromatic vinyl compounds, e.g., styrene and α-methyl styrene, can be used.

As another manufacturing method, a specific phosphonate monoester metal compound can be dissolved or dispersed into an appropriate solvent. In these methods, a dissolution assistant may be added in order to promote the dissolving of the metal compound acting as a metal ion source into the phosphonate monoester compound or solvent.

Though dependable on the species of solvent used, the use or purpose of the optical member, and the like, the content of the specific phosphonate monoester metal compound contained in the liquid composition is usually adjusted so as to fall within the range of 0.1 to 1900 parts by mass, preferably 1 to 900 parts by mass, particularly preferably 5 to 400 parts by mass, with respect to 100 parts by mass of solvent from the viewpoint of viscosity after formulation.

Third Embodiment

The optical material of this embodiment is a composition in which a specific phosphonate monoester metal compound is contained in a resin. The specific phosphonate monoester metal compound is excellent in its compatibility with the resin, so that the metal ion can favorably be dispersed into the resin. The resin is not restricted in particular as long as it is a resin excellent in compatibility or dispersibility with the phosphonate monoester compound and/or specific phosphonate monoester metal compound. As such a resin, resins such as the acrylic resin shown in the following, for example, can be used favorably.

As the acrylic resin, (meth) acrylate ester type monomers or polymers obtained there from are used preferably. Specific examples of (meth) acrylate ester type monomer having a single functional group include alkyl (meth)acrylates such as methyl (meth) acrylate, ethyl (meth)acrylate, n-propyl (meth)acrylate, n-butyl (meth)acrylate, isobutyl (meth) acrylate, tertiary butyl (meth)acrylate, n-hexyl (meth) acrylate, and n-octyl (meth) acrylate; modified (meth) acrylates such as glycidyl (meth)acrylate, 2-hydroxyethyl (meth) acrylate, 2-hydroxypropyl (meth)acrylate, hydroxybutyl (meth)acrylate, isobornyl (meth)acrylate, methoxy polyethylene (meth) acrylate, and phenoxy (meth) acrylate; polyfunctional (meth)acrylates such as ethylene glycol di(meth) acrylate, diethylene glycol di(meth)acrylate, polyethylene glycol di (meth) acrylate, polypropylene glycol di(meth) acrylate, 1,3-butylene glycol di(meth)acrylate, 1,4-butanediol di(meth)acrylate, 1,6-hexanediol di(meth) acrylate, neopentyl glycol di(meth)acrylate, 2-hydroxy-1,3-di(meth)acrylate, 2,2-bis[4-(meth)acryloxyethoxyphenyl] propane, 2-hydroxy-1-(meth)acryloxy-3-(meth) acryloethoxyphenyl] propane, trimethylol propane tri(meth) acrylate, pentaerythritol tri(meth)acrylate, and pentaerythritol tetra(meth)acrylate.

As another resin, a combination of the above-mentioned (meth)acrylate ester type monomer and another copolymerizable monomer which can copolymerize with this (meth) acrylate ester type monomer may be used. Specific examples of such a copolymerizable monomer include unsaturated carboxylic acids such as (meth)acrylic acid, 2-(meth) acryloyl oxyethyl succinic acid, and 2-(meth) acryloyl oxyethyl phthalic acid; acrylamides such as N,N-dimethyl acrylamide; and aromatic vinyl compounds such as styrene, α-methyl styrene, chlorostyrene, dibromostyrene, methoxystyrene, vinyl benzoic acid, and hydroxymethyl styrene.

Examples of the resin polymer include polyethylene terephthalate (PET), polyethylene, polypropylene, polyvinyl chloride, various polycarbonate esters (polycarbonates), various polyurethanes, various epoxy resins, and the like. They further include polymers of aromatic vinyl compounds such as styrene, α-methyl styrene, chlorostyrene, dibromostyrene, methoxystyrene, vinyl benzoic acid, hydroxymethyl styrene, and divinyl benzene.

If monofunctional monomers are used alone as monomers constituting a resin, thermoplastic molded articles will be obtained as those polymerized. If polyfunctional ones are used as a part or all of the monomers, thermosetting molded articles are obtained. Therefore, when these resins are selected appropriately, molded articles of optical materials or optical materials corresponding to the purpose, use, molding processing method, and the like can be obtained. If thermoplastic ones are used, then the re-forming after polymerization becomes easier, thereby improving the molding processability.

Though specific methods for preparing the resin composition are not restricted in particular, the following two methods and the like are preferable.

First Preparing Method: This method is a method in which the phosphonate monoester compound and the metal ion source or a specific phosphonate monoester metal compound obtained upon their reaction is contained in a monomer, so as to prepare a monomer composition. This monomer composition can be used as an optical material as it is without polymerization. Alternatively, the monomer composition may be radically polymerized to yield an optical material.

In this method, as specific techniques for radically polymerizing the monomer composition, radical polymerization techniques using a normal radical polymerization initiator, e.g., known techniques such as cast polymerization, suspension polymerization, emulsion polymerization, and solution polymerization can be utilized. However, the polymerization techniques should not be restricted to these. From the viewpoints of improving the resistances to weather and heat in the molded article of the optical material obtained upon the polymerization of the monomer composition, it will be preferred if various additives for polymers such as UV-absorbing agent and light stabilizer are added to the monomer composition. Also, various colorants may be added thereto in order to adjust the color tone of the optical material.

Examples of such a UV absorbing agent include those of salicylate type such as p-tert-butylphenyl salicylate; benzophenone type such as 2,4-dihydroxy benzophenone and 2-hydroxy-4-methoxy benzophenone; benzotriazole type such as 2-(2'-hydroxy-3'-tert-butyl-5'-methylphenyl)-5-chlorobenzotriazole and 2-(2'-hydroxy-5'-octylphenyl)benzotriazole; and cyanoacrylate type such as ethyl-2-cyano-3,3-diphenyl acrylate.

Examples of the light stabilizer usable include various hindered amine type light stabilizers such as dimethyl succinate polymers with bis(1,2,2,6,6-pentamethyl-4-piperidyl) cebacate, bis(2,2,6,6-tetramethyl-4-piperydyl) cebacate, di(1,2,2,6,6-pentamethyl-4-piperidyl)-butyl(3',5'-diter t-butyl-4-hydroxybenzyl) malonate, 1-(2-(3-(3,5-ditert-butyl-4-hydroxyphenyl)propionyloxy) ethyl)-4-(3-(3,5-ditert-butyl-4-hydroxyphenyl)propionyl oxy)-2,2,6,6-tetramethyl piperidine, poly{(6-{1,1,3,3-tetramethylbutyl} amino)-1,3,5-triazine-2, 4-diyl}(1,6-{2,2,6,6-tetramethyl-4-piperidinyl} aminohexamethylene)}, poly{{6-(morpholino)-S-triazine-2,4-diyl}{1,6-(2,2,6,6-tetramethyl-4-piperidinyl)amino}hexametylene}, and 4-hydroxy-2,2,6,6-tetramethyl-1-piperidinetanol.

As the radical polymerization initiator, normal organic peroxide type polymerization initiators can be used. Preferably usable are peroxyesters such as tert-butyl peroxy neodecanoate, tert-butyl peroxydecanate, tert-butyl peroxy pivalate, tert-butyl peroxy benzoate, tert-butyl peroxy-2-ethyl hexanoate, tert-butyl peroxy laurate, and tert-butyl peroxy-3,5,5-trimethyl hexanoate; diacyl peroxides such as lauroyl peroxide and 3,5,5-trimethyl hexanoyl peroxide; and peroxy ketals such as 1,1-bis(tert-butyl peroxy)-3,5,5-trimethyl cyclohexane.

Also, azo type radical polymerization initiators such as 2,2-azobis(isobutyronitrile), 2,2'-azobis(2,4-dimethyl valeronitrile), and 1,1'-azobis(cyclohexane-2-carbonitrile) are used favorably.

Second Preparing Method: This method is a method in which the phosphonate monoester compound and the metal ion source or a specific phosphonate monoester metal compound obtained upon their reaction is added to and mixed with a resin. This method is effectively utilized when a thermoplastic resin is used as the resin. Specific examples are the following two methods:

(1) A method in which the phosphonate monoester compound represented by formula (1) and the metal ion source or the specific phosphonate monoester metal compound is added to a molten resin, and the mixture is kneaded.

(2) A method in which the resin is dissolved or dispersed into or swollen with an appropriate organic solvent, the phosphonate monoester compound represented by formula (1) and the metal ion source or the specific phosphonate monoester metal compound is added to and mixed with the resulting solution, and then the organic solvent is eliminated from the solution.

In each of the above-mentioned methods, there are cases where the addition of various dissolution assistants is effective in enhancing the solubility of the metal ion source. Therefore, such processing is preferable.

In the two preparing methods, examples of the kneading means in the former method (method of (1)) include those generally used in melting and kneading methods for thermoplastic resins, e.g., means in which melting and kneading are effected by use of a mixing roll, and means in which an extruder is used for melting and kneading after preliminary mixing by use of a Henschel mixer or the like.

On the other hand, the organic solvent used in the latter method (method of (2)) is not limited in particular as long as it can dissolve or disperse the resin or can be swollen with the resin. Specific examples include alcohols such as methyl alcohol, ethyl alcohol, and isopropyl alcohol; ketones such as acetone and methyl ethyl ketone; aromatic hydrocarbons such as benzene, toluene, and xylene; chlorine type hydrocarbons such as methylene chloride; and amide compounds such as dimethyl acrylamide and dimethyl formamide.

Here, though dependable on the use and purpose of the optical material, the content of the specific phosphonate monoester metal compound in the optical material in this embodiment, i.e., in the resin composition, is adjusted so as to fall within the range of 0.1 to 400 parts by mass in general, preferably 0.3 to 200 parts by mass, particularly preferably 1 to 100 parts by mass, with respect to 100 parts by mass of the resin from the viewpoint of formability. As mentioned above, the content of metal ion in the resin composition is adjusted so as to fall within 0.01% to 60% by mass with respect to the whole resin composition.

Fourth Embodiment

The optical material in accordance with this embodiment is a mode of a resin composition in which a specific phosphonate monoester metal composition is contained in a resin having an adherence (hereinafter referred to as "adhesive resin"). Examples of such an adhesive resin include adhesive acrylic resins, polyvinyl butyral, ethylene/vinyl acetate copolymer or its partially saponified products, and the like. The adhesive composition of this embodiment is obtained when the phosphonate monoester compound represented by formula (1) and the metal ion source or the specific phosphonate monoester metal compound is mixed with these adhesive resins.

The adhesive composition can further contain a UV-absorbing agent of benzotriazole type, benzophenone type, or salicylic acid type, antioxidants, stabilizers, and the like. It can further contain various plasticizers. Examples of such plasticizers include phosphate ester type plasticizers such as tricresyl phosphate and triphenyl phosphate; phthalate type plasticizers such as dioctyl phthalate and dibutyl phthalate; aliphatic acid type plasticizers such as dibutyl cebacate, butyl ricinolate, methyl acetyl ricinolate, and butyl succinate; and glycol type plasticizers such as butyl phthalyl butyl glycolate, triethylen glycol dibutylate, triethylene glycol di-2-ethyl butyral, and polyethylene glycol.

In the optical material of the present invention explained in the foregoing, an oxygen atom derived from the hydroxyl group of the phosphonate monoester compound is combined with the metal ion by a coordinate bond or ionic bond. Thus, the metal ion is dissolved or dispersed in the composition while in a state surrounded by phosphonate groups, whereby an absorption characteristic or emission characteristic peculiar to the atomic structure of the metal (ion) employed is expressed favorably. Therefore, an optical material having an optical characteristic corresponding to the absorption characteristic, transmission characteristic, or emission characteristic of the metal ion can be obtained.

When the phosphonate monoester compound represented by formula (1) is contained together with the copper ion, the compatibility with the resin improves as compared with that obtained conventionally. Hence, the transparency remarkably improves when the phosphonate monoester copper compound is contained in the resin so as to form a resin-made optical member such as a resin board. Also, the compatibility of the phosphonate monoester copper compound with the resin improves, whereby the dispersibility of the metal ion into the resin can be improved as compared with that obtained conventionally.

Though details of operating mechanisms by which the compatibility with the resin is improved as such have not fully been elucidated yet, they are presumed to be due to the following reason, for example. Namely, it is presumed to be because of the fact that the phosphorus atom in the phosphate monoester compound or at least one of groups of $R^1$ and $R^2$ in formula (1) combined with the oxygen atom combined with the phosphorus atom is substituted by a functional group, whereby the polarity balance changes in a mixed system containing the phosphonate monoester compound, copper ion, and resin, or the free energy of the system changes. However, the operation is not restricted thereto.

It has also been verified that the optical material in accordance with the present invention not only improves the transparency when formed into a resin article, but also significantly expands the transmission wavelength region (range), i.e., the width of so-called "visible transmission window," when the copper ion is used as the metal ion. At present, it has not yet been elucidated in detail whether this is caused by the improvement in compatibility with the resin or other major reasons. Further, it has been verified that the optical material in accordance with the present invention improves its heat resistance as compared with conventional ones using a phosphate ester compound and those using a phosphinate compound. Also, it has been elucidated that the solubility or dissolution stability with respect to the monomer constituting the resin is remarkably improved as compared with the conventional ones using a phosphonate compound.

Though there are many unclear points concerning the reason why these effects are exhibited, the heat resistance improves, so that thermal decomposition is hard to occur at the time of thermoforming during which heat is applied, whereby molding processability can be improved when making the resin-made optical member, for example. Since the solubility or dissolution stability with respect to the monomer constituting the resin improves, it is advantageous in that resin-made optical members such as a practically usable optical filter and the like are easier to form.

Further, optical materials with better optical functions can be obtained when, among the metal ions mentioned above, ions of sodium, potassium, magnesium, calcium, iron, manganese, nickel, cobalt, copper, neodymium, praseodymium, europium, thulium, erbium, terbium, dysprosium, samarium, and holmium are used. In particular, copper can express quite excellent near-infrared light absorption characteristics and visible light transmission characteristics when coordinated or combined with the phosphonate monoester compound, whereby it can be formed into an optical material suitable for various uses such as luminosity correction, photometry, near-infrared light and infrared light cutoff, heat ray absorption, luminance adjustment, and the like.

On the other hand, neodymium, praseodymium, europium, thulium, erbium, terbium, dysprosium, samarium, and holmium have large, steep absorption wavelength peaks. Also, they are excellent in wavelength component selectivity and tend to yield a higher fluorescent emission efficiency or emits laser. Therefore, optical materials suitable for various uses such as luminosity correction, optical amplification, and protective shielding can be formed.

When the optical material of the present invention is in the form of the liquid composition or resin composition as mentioned above, characteristics and properties corresponding to solvents and resins can be imparted to the optical material or the optical member resulting from the optical material. Therefore, if the solvents and resins are selected appropriately, then highly functional optical materials suitable for various uses can be manufactured easily and securely.

Furthermore, since the optical material can have various forms (the specific phosphonate monoester metal compound itself, liquid composition, resin composition, adhesive composition, and the like), excellent characteristics, e.g., molding processability, thermoplasticity, theremocurability, transparency, resistance to weather, lightness in weight, adherence, easiness in handling, easiness in coating, and drying property, corresponding to each form can be imparted to the optical material and/or the optical member obtained therefrom. Therefore, optical materials with a high versatility employable in various uses can be obtained.

Optical Member

When the optical material in accordance with the present invention is used, optical members suitable for various uses can be formed. Examples of modes of optical members include the optical material itself, those combined with a light-transparent material and the like, those molded, and the like. Specifically, they may have various forms such as powder, liquid, adhesive, paint, film, sheet, tube, and lens.

Such an optical member is suitable for constituting luminosity correction members for CCD, CMOS, or other light-receiving devices, luminosity correcting members, photometric members, heat ray absorbing members, complex optical filters, lens members (e.g., glasses, sunglasses, goggles, optical systems, and optical waveguide systems), fiber members (optical fibers), noise-cutting members, display covers or display filters for plasma display faceplates, projector faceplates, light source heat ray cutting members, color tone correcting members, illumination brightness regulating members, optical devices (optical amplifier devices, wavelength converter devices, and the like), Faraday devices, optical communication function devices such as isolators, optical disk devices, and the like due to its excellent durability, weather resistance, optical characteristics, versatility, economy, molding processability, and the like.

EXAMPLES

Specific examples concerning the present invention will now be explained, which do not restrict the present invention.

Example 1

Into 96.0 g of methyl methacrylate (hereinafter referred to as "MMA"), 1.98 g of monoethyl 3-methoxy butyl phosphonate represented by the above-mentioned expression (3) were dissolved. With 1.0 g of copper acetate monohydrate added thereto, the mixture was heated so as to attain an internal temperature of 80° C. and was stirred for 2 hours. After the mixture was uniformly dissolved, the solvent and acetic acid generated as a byproduct were evaporated, whereby a solid was obtained. The solid was dried under vacuum for one night at 40° C., whereby a copper complex was prepared. This copper complex is a phosphonate monoester copper compound as the optical material in accordance with the present invention.

Comparative Example 1

A copper complex was obtained in the same manner as Example 1 except that 2.97 g of 2-ethylhexyl-2-ethylhexyl phosphonate (PC-88A, manufactured by Daihachi Chemical Industry Co., Ltd.) represented by the following expression (4) were used in place of monoethyl 3-methoxy butyl phosphonate.

(4)

Comparative Example 2

A copper complex was obtained in the same manner as Example 1 except that 98.0 g of MMA, 0.314 g of copper acetate monohydrate, and 0.92 g of di (2-ethylhexyl) phosphinic acid represented by the following expression (5) in place of monoethyl 3-methoxy butyl phosphonate were used.

(5)

Comparative Example 3

A copper complex was obtained in the same manner as Example 2 except that 0.914 g of di (1,1,3,3-tetramethylbutyl) phosphinic acid (Phoster, manufactured by Nippon Chemical Industrial Co., Ltd.) is represented by the following expression (6) was used in place of di(2-ethylhexyl) phosphinic acid.

(6)

Spectral Characteristic Evaluation Test

Each of the copper complexes obtained by Example 1 and Comparative Examples 1 to 3 was dissolved in MMA so as to yield a copper ion concentration of 0.1 wt %. The spectral absorbance of each of thus obtained solutions over the wavelength range of 250 to 1200 nm was measured by use of a spectrophotometer "U-4000" (manufactured by Hitachi, Ltd.). The formulations of the copper complexes and MMA are as follows:

0.71 g of copper complex of Example 1 with 99.29 g of MMA;

1.06 g of copper complex of Comparative Example 1 with 98.94 g of MMA;

1.01 g of copper complex of Comparative Example 2 with 98.99 g of MMA; and 1.01 g of copper complex of Comparative Example 3 with 98.99 g of MMA.

As mentioned above, FIG. 1 is a graph showing optical absorption spectra of the respective MMA solutions of copper complexes of Example 1 and Comparative Examples 1 to 3. Curves L1 to L4 in the graph show results concerning the respective MMA solutions of Example 1 and Comparative Examples 1 to 3.

Figure 1:
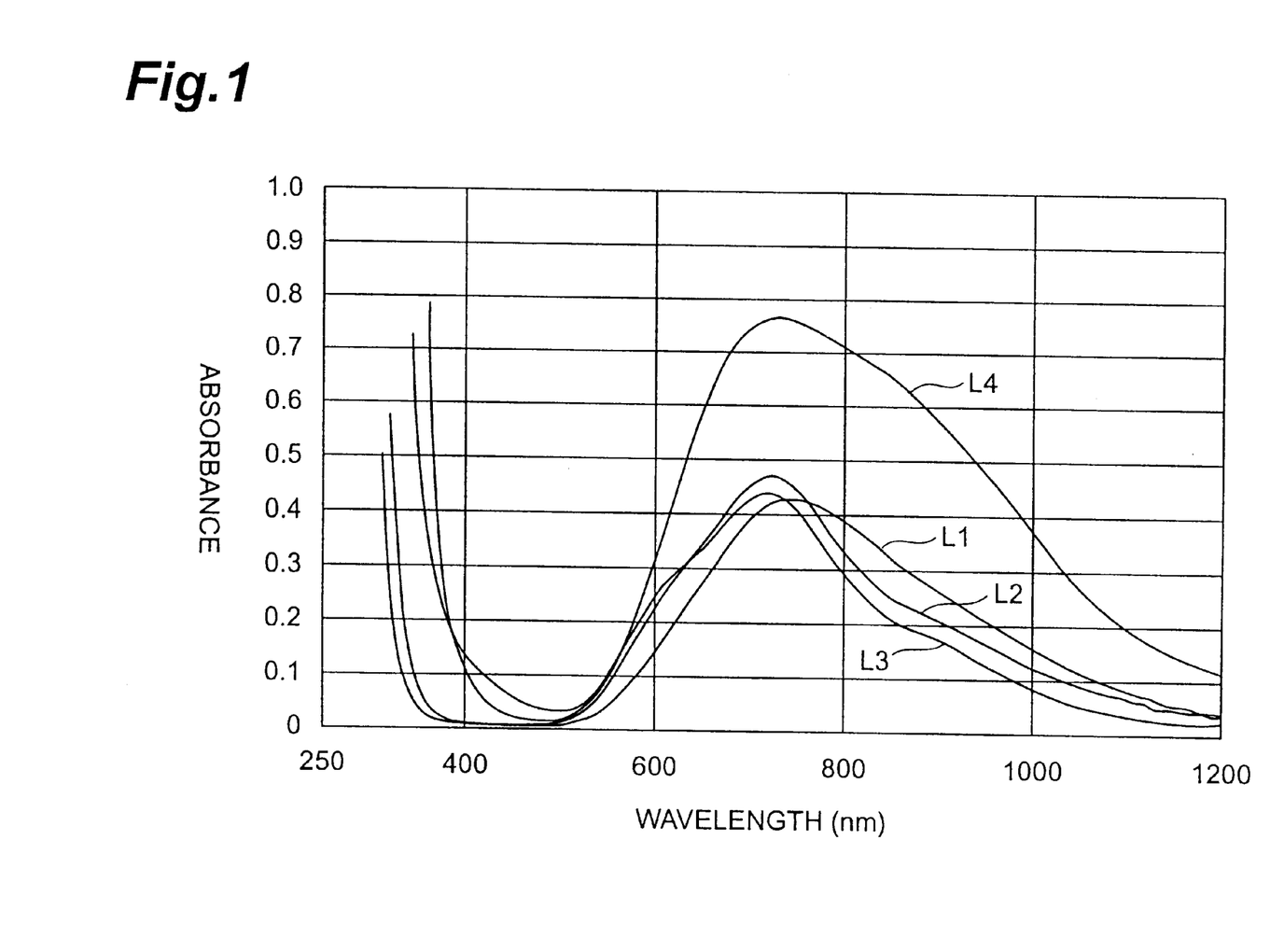
FIG. 1 is a graph showing the optical absorption spectra for MMA solutions of copper complexes of Example 1 and Comparative Examples 1 to 3.

From these results, it has been verified that, as compared with the copper complexes of Comparative Examples 1 to 3, which are conventional optical materials, the copper complex of Example 1, which is the optical material of the present invention, exhibits a lower absorbance on the shorter and longer wavelength sides of the visible region, namely, the transmission window of the visible region is widened.

In particular, while coloring in a yellow region has been seen by a visual inspection as well in the MMA solutions of the copper complexes using Comparative Examples 2 and 3 corresponding to curves L3 and L4, no such coloring has been seen in the MMA solution of the copper complex of Example 1. It has also been seen that the maximum wavelength of absorbance in the near-infrared region shifts to the longer wavelength side in the MMA solution of the copper complex of Example 1. Such a spectral characteristic of the copper complex of Example 1 is quite suitable for the above-mentioned optical members for various uses.

Heat Resistance Evaluation Test 1

The copper complexes obtained by Example 1 and Comparative Examples 1 to 3 were heated at 230° C. for 10 minutes. The heated copper complexes were dissolved in MMA as in the above-mentioned "Spectral Characteristic Evaluation Test," and spectral absorbance was measured. As mentioned above, FIGS. 2 to 4 are graphs showing optical absorbance spectra of the copper complexes of Example 1 and Comparative Examples 2 and 3 (in the state dissolved in MMA) before and after heating, respectively.

Figure 2:
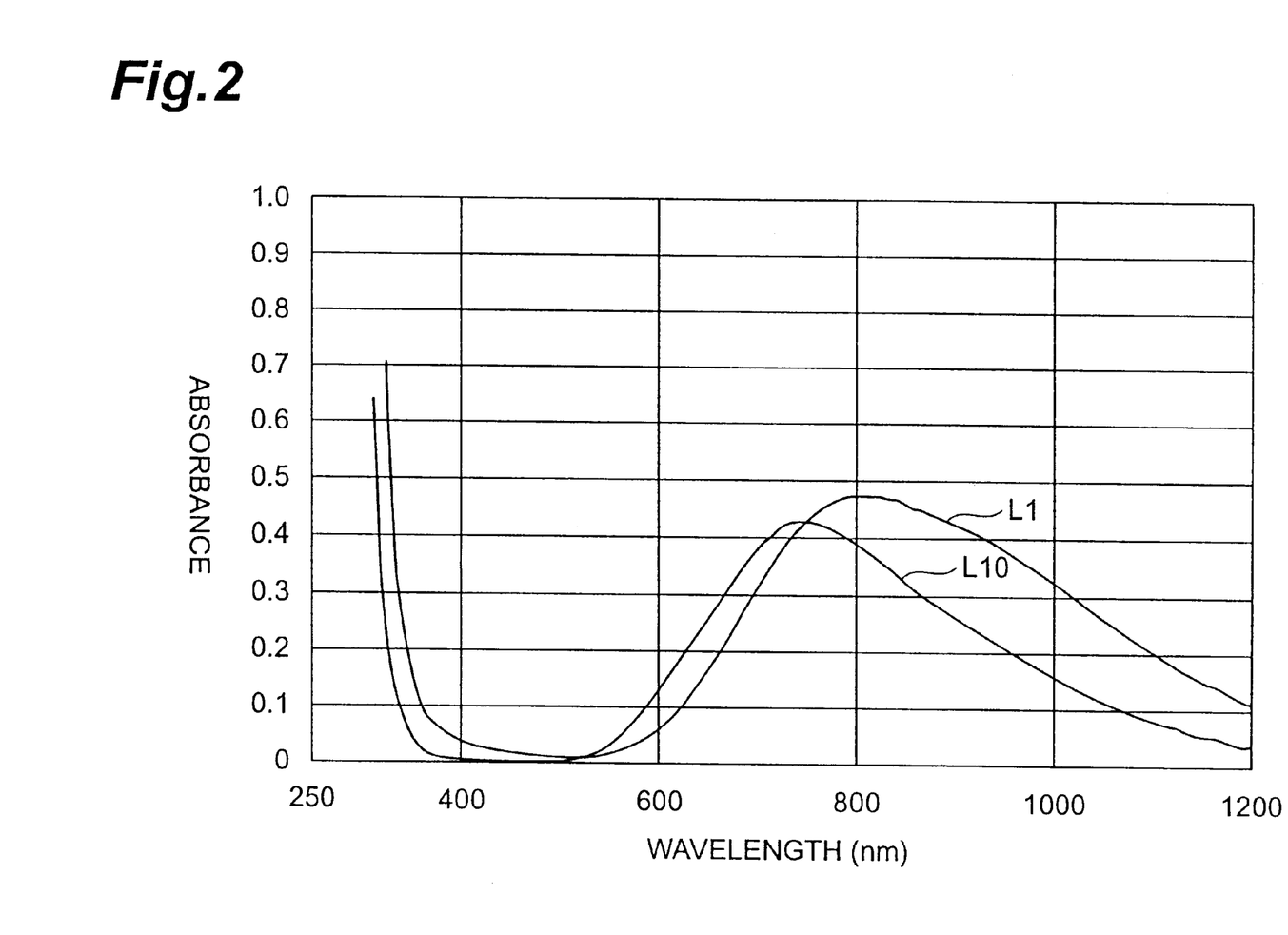
FIG. 2 is a graph showing the optical absorption spectra for the copper complex of Example 1 (in the state dissolved in MMA) before and after heating.
Figure 3:
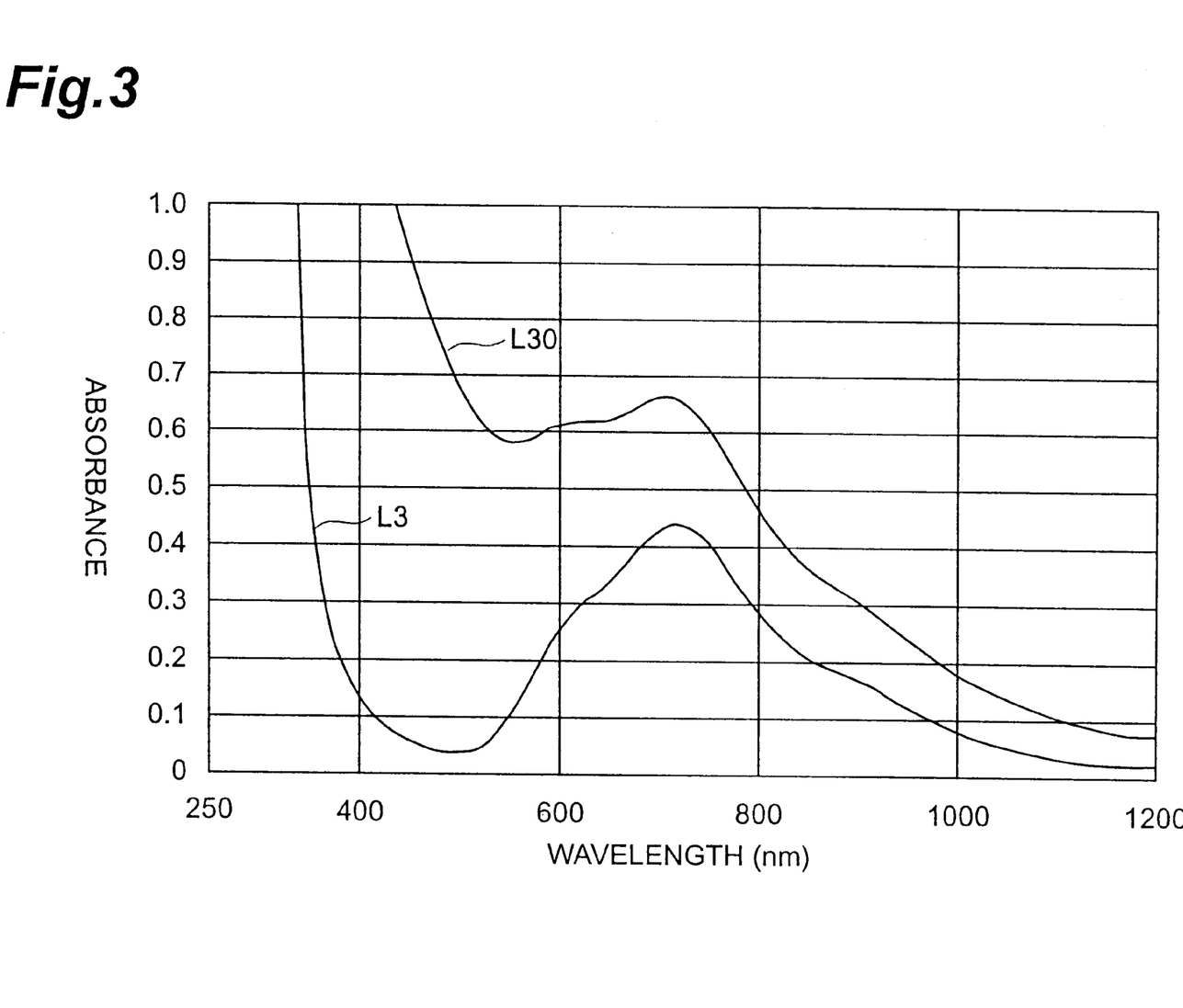
FIG. 3 is a graph showing the optical absorption spectra for the copper complex of Comparative Example 2 (in the state dissolved in MMA) before and after heating.
Figure 4:
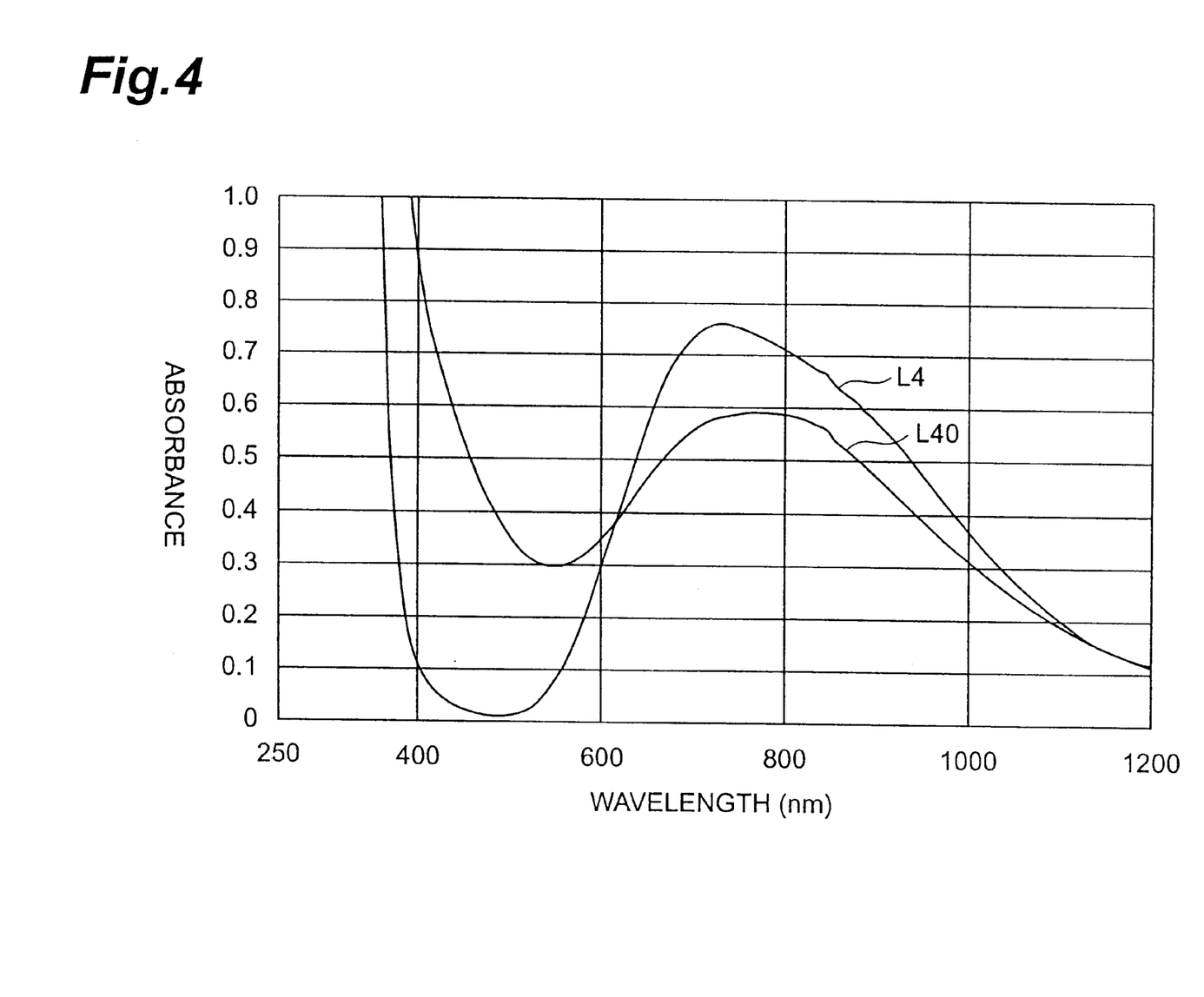
FIG. 4 is a graph showing the optical absorption spectra is for the copper complex of Comparative Example 3 (in the state dissolved in MMA) before and after heating.

Curves L1, L3, and L4 in FIGS. 2 to 4 indicate optical spectra before heating (which are identical to curves L1, L, and L4 in FIG. 1), where as curves L10, L30, and L40 indicate optical spectra after heating.

FIG. 2 proves that the copper complex (optical material) of Example 1 in accordance with the present invention maintains sufficient visible light transmission and near-infrared light absorbance characteristics without greatly changing its spectral form though the optical spectrum slightly shifts toward the shorter wavelength side between before and after heating. As a consequence, this copper complex is seen to be excellent in heat resistance (heat stability). By contrast, it is seen that the absorbance in the visible region increases enormously in the copper complexes of Comparative Examples 2 and 3 between before and after heating, whereby their heat resistance is not sufficient as compared with that of the optical material of the present invention.

Comparative Example 4

Into 18.0 g of toluene, 0.32 g of phosphate ester compound represented by the following formula (7) and 0.45 g of the phosphate ester compound represented by the following formula (8) were dissolved. With 0.50 g of copper acetate monohydrate added thereto, the mixture was heated so as to attain an internal temperature of 60° C., and the mixture was stirred for 2 hours in this state. After the completion of the reaction, the reaction solvent and acetic acid generated as a byproduct were evaporated, and the residue was dried under vacuum for one night at 40° C., whereby a copper complex was obtained.

Heat Resistance Evaluation Test 2

Pyrolysis characteristics of the copper complexes obtained by Example 1 and Comparative Example 4 were measured by the following measurement apparatus under the following measurement condition:

a) Measurement Apparatus: TA4000 thermal analysis system manufactured by Mettler b) Measurement Condition: a heating rate of 10° C./min over a temperature range of 30° C. to 300° C. in a nitrogen atmosphere. Table 1 shows the results of measurement of temperatures (pyrolysis temperatures) at which the weight decreased by 1% and 5%, respectively, from that before heating. From the table, it is seen that the thermal stability of the copper complex (optical material) of Example 1 in accordance with the present invention is much higher than that of the copper complex of Comparative Example 4 using the conventional phosphate ester compound.

TABLE 1

| | Pyrolysis temperature (° C.) | |
|---|---|---|
| | 1% weight loss | 5% weight loss |
| Example 1 | 171 | 226 |
| Comparative Example 4 | 83 | 185 |

Heat Resistance Evaluation Test 3

Each of the copper complexes obtained in Example 1 and Comparative Example 4 was mixed with heated polymethacrylate (hereinafter referred to as "PMMA") beads so as to be kneaded therein, and the mixture was formed into a sheet-like optical member (having a thickness of 3 mm). The heating condition was at 175° C. for 4 minutes. After the sheet-like articles were cooled to room temperature, their spectral transmissivity over the wavelength range of 250 to 1200 nm was measured by using a spectrophotometer "U-4000" (manufactured by Hitachi, Ltd.).

Figure 5:
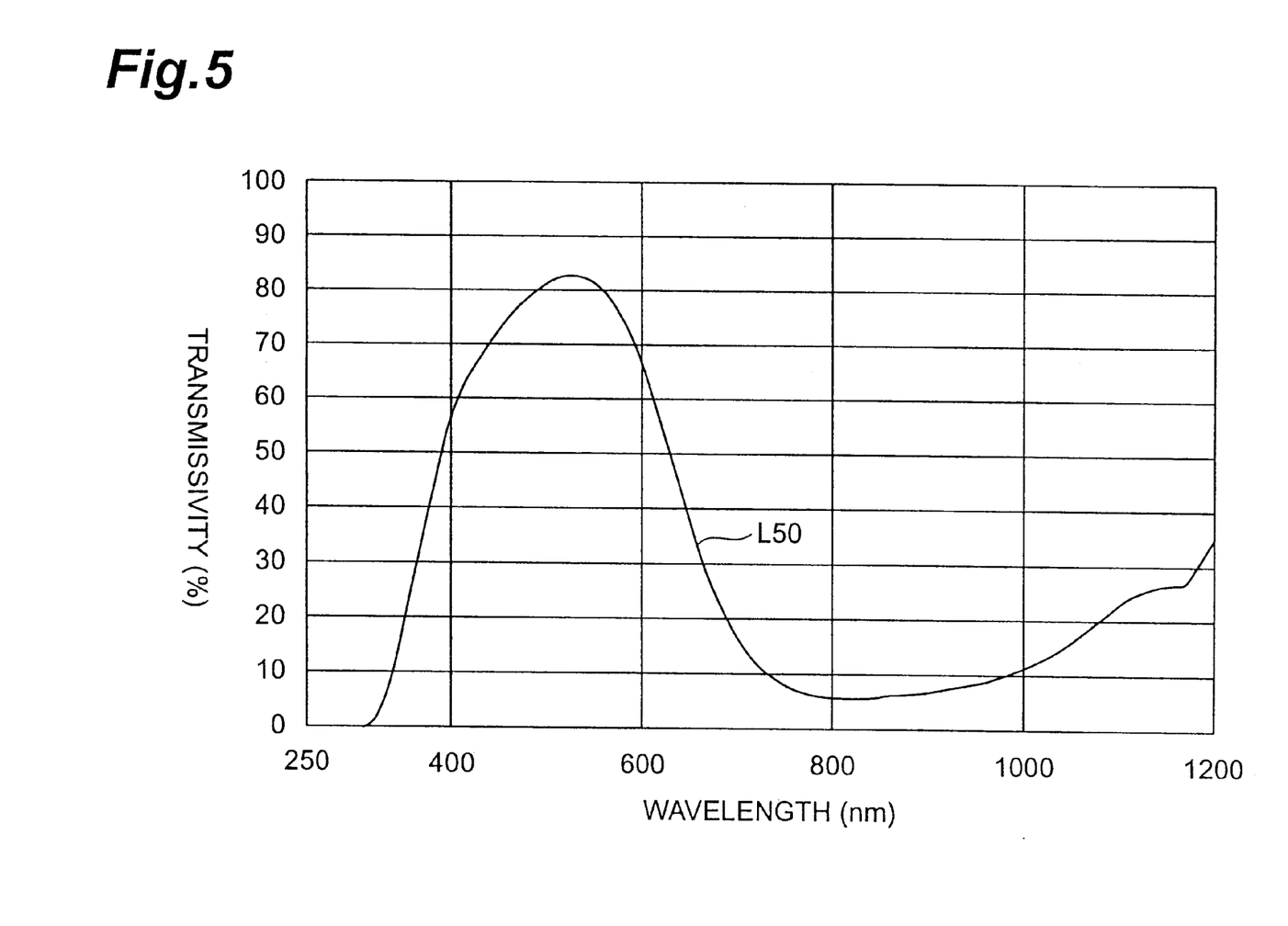
FIG. 5 is a graph showing the optical transmission spectrum for the copper complex of Example 1 (in the state kneaded in PMMA)
Figure 6:
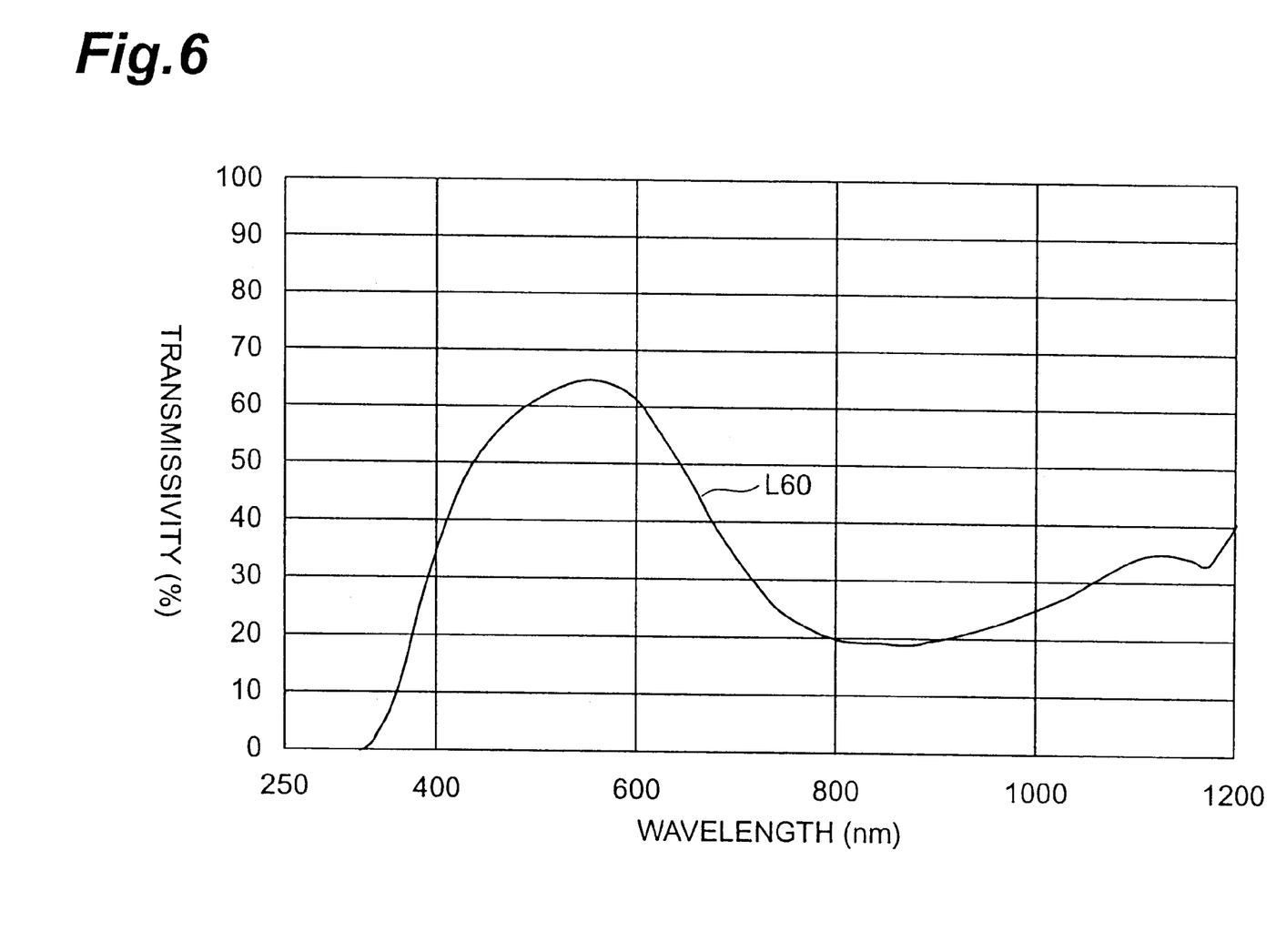
FIG. 6 is a graph showing the optical transmission spectrum for the copper complex of Comparative Example 4 (in the state kneaded in PMMA).

FIGS. 5 and 6 are graphs showing optical transmission spectra of the copper complexes in accordance with Example 1 and Comparative Example 4 (in the state kneaded into PMMA). These results also verify that the copper complex of Example 1 in accordance with the present invention exhibits a thermal stability higher than that of the copper complex of Comparative Example 4 using the conventional phosphate ester compound. Since the copper complex of Example 1 in accordance with the present invention has a sufficient spectral characteristic even when mixed with the heated resin as such, it is found very effective for manufacturing methods, e.g., extrusion molding using a thermoplastic resin.

Comparative Example 5

Into 18.0 g of tetrahydrofuran, 0.91 g of ethyl phosphonic acid was dissolved. With 0.50 g of copper acetate anhydride added thereto, the mixture was stirred for 2 hours in the state heated so as to attain an internal temperature of 60° C. The precipitate was filtered out and dried under vacuum for one night at 40° C., whereby a copper complex was obtained. When 1.14 g of this copper complex was mixed with 98.86 g of MMA and 0.20 g of α-methyl styrene, the copper complex did not sufficiently dissolve in MMA, thus yielding a suspended state. To this suspension, 1.00 g of t-butyl peroxy decanate was added as a radical initiator. The resulting mixture was polymerized as being successively heated to different temperatures of 45° C. for 16 hours, 60° C. for 8 hours, and 100° C. for 3 hours, whereby a resin molded article having a thickness of 3 mm was obtained.

When this resin molded article was visually observed, granular precipitates were seen within matrices of the resin. When the optical spectrum of the resin molded article was measured, the part having a relatively large amount of precipitate exhibited a high absorbance over the whole wavelength range from visible to near infrared. The absorption of near-infrared light was insufficient in the part having a relatively small amount of precipitate, so that the optical spectrum exhibited an obtuse form as a whole.

As explained in the foregoing, the optical material of the present invention can express an excellent absorption characteristic or emission characteristic for specific wavelength light, and can improve the compatibility with resins as compared with conventional ones. Also, since the compatibility with resins is improved as such, the use of the optical material in accordance with the present invention makes it possible to yield a resin-made optical member whose transparency is fully improved. Further, the optical material of the present invention makes it possible to yield a resin-made optical member whose optical characteristics (spectral characteristics) are improved as well.

From the invention thus described, it will be obvious that the embodiments of the invention may be varied in many ways. Such variations are not to be regarded as a departure from the spirit and scope of the invention, and all such modifications as would be obvious to one skilled in the art are intended for inclusion within the scope of the following claims.

What is claimed is:

1. An optical material having an absorption characteristic or emission characteristic peculiar to atomic structure of a metal ion and containing a phosphonate monoester compound represented by the following formula (1) and said metal ion:

(1)

wherein R¹ indicates a branched, linear, or annular alkyl, alkenyl, alkynyl, aryl, or allyl group whose carbon number is 1 to 30;

wherein R² indicates a branched, linear, or annular alkyl, alkenyl, alkynyl, aryl, or allyl group whose carbon number is 1 to 30;

wherein at least one of R¹ and R² has at least one hydrogen atom substituted by a halogen atom, an oxyalkyl group, a polyoxyalkyl group, an oxyaryl group, a polyoxyaryl group, an acyl group, an aldehyde group, a carboxyl group, a hydroxyl group, a (meth)acryloyl group, a (meth)acryloyloxyalkyl group, a (meth)acryloylpolyoxyalkyl group, or an ester group.

2. An optical material according to claim 1, wherein said metal ion is an ion of at least one metal of iron, manganese, nickel, cobalt, chromium, copper, neodymium, praseodymium, europium, thulium, erbium, terbium, dysprosium, samarium, lanthanum, gadolinium, and holmium.

3. An optical material according to claim 1, wherein said phosphate monoester compound and said metal ion are contained in a solvent or a resin.

* * * * *